United States Patent [19]

Vanderpool

[11] 4,218,403

[45] Aug. 19, 1980

[54] SYNTHESIS OF AROMATIC ALDEHYDES

[75] Inventor: Steven H. Vanderpool, Austin, Tex.

[73] Assignee: Texaco Development Corporation, White Plains, N.Y.

[21] Appl. No.: 27,580

[22] Filed: Apr. 6, 1979

[51] Int. Cl.² ............................................. C07C 45/02
[52] U.S. Cl. .................................................... 568/428
[58] Field of Search ........................................ 260/599

[56] References Cited

U.S. PATENT DOCUMENTS

| | | | |
|---|---|---|---|
| 1,989,700 | 2/1935 | Larson | 260/599 |
| 2,485,237 | 10/1949 | Gresham et al. | 260/599 |

*Primary Examiner*—Bernard Helfin
*Attorney, Agent, or Firm*—Carl G. Ries; Robert A. Kulason; James L. Bailey

[57] ABSTRACT

Covers a method for preparing a para-alkyl substituted phenyl aldehyde by reacting carbon monoxide and an alkyl mono-substituted benzene in presence of a tantalum, niobium or antimony pentafluoride-hydrogen fluoride catalyst.

9 Claims, No Drawings

SYNTHESIS OF AROMATIC ALDEHYDES

BACKGROUND OF THE INVENTION

1. Field of the Invention

The present invention relates to a process of producing an aromatic aldehyde such as p-tolualdehyde by reacting the appropriate alkylbenzene with carbon monoxide in presence of a Ta, Nb, or Sb pentafluoride-hydrogen fluoride catalyst system.

A number of processes have been proposed to produce aromatic aldehydes such as para-tolualdehyde. For the most part, these methods involve reacting the alkyl-substituted benzene, such as toluene with carbon monoxide in presence of some type of a catalyst system. However, while such methods have proven to be useful, they suffer from one or more process deficiencies. For example, in some instances processes of this type necessarily involve resort to subambient temperatures, which, of course, involves some considerable process control. In other cases, large excesses of catalyst must necessarily be employed to carry out the synthesis to obtain appreciable yields. In still other instances, useful catalysts in this reaction are highly corrosive leading to obvious problems. Lastly, in some cases, the reaction is effected only at relatively high pressures.

Typical prior art references involving carbonylation of aromatic hydrocarbons such as toulene include U.S. Pat. Nos. 1,197,682; 2,485,237; and 3,948,998 and German Patent Nos. 2,422,197; and 2,460,673; and British Patent No. 1,422,308.

It therefore becomes an object of the invention to provide a process for producing aromatic aldehydes such as para-tolualdehyde by means which eliminate the above discussed disadvantages and others.

Other objects will appear hereinafter.

SUMMARY OF THE INVENTION

In brief, the present invention provides a method for preparing a para-alkyl mono-substituted phenylaldehyde by reacting under super atmospheric pressure carbon monoxide and an alkyl-substituted benzene in presence of a catalyst system. The catalyst comprises hydrogen fluoride and a pentafluoride selected from the group consisting of $TaF_5$, $NbF_5$, and $SbF_5$.

DETAILED DESCRIPTION OF THE INVENTION

The alkyl-substituted aromatic hydrocarbons which may be used here include toluene, ethylbenzene, propylbenzene, butylbenzene, hexylbenzene, etc. The alkyl group attached to the aromatic ring may contain as many as eighteen carbon atoms. It is preferred that the alkyl substitutent contain twelve or less carbon atoms and most preferably is $C_6$ or less. In a greatly preferred practice of the invention toluene is the reactant here.

The alkyl-substituted aromatic hydrocarbon to be carbonylated is usually first mixed with the catalyst prior to introduction into the reaction vessel. Thereafter, carbon monoxide is introduced under pressure. The catalyst-alkyl-substituted aromatic reactant may be dissolved in an extraneous solvent, or excesses of the aromatic hydrocarbon to be carbonylated may be employed, which excesses act as a solvating medium. Thus, any solvent may be employed which essentially is inert to the carbon monoxide reaction under conditions stated herein. Preferably the alkyl-substituted aromatic to be carbonylated is used in excess as a solvent.

The amounts of catalyst used in relation to the alkyl-substituted aromatic reactant may vary widely. Usually about 1–5 moles of pentafluoride catalyst per mole of alkyl-substituted benzene is employed. More often the ratio is 1–2 moles of pentafluoride per mole of reactant, with the most preferred ratio being 1:1.

With relation to the hydrogen fluoride cocatalyst usually at least 5 moles of hydrogen fluoride per mole of alkyl-substituted benzene reactant is employed. Most typically 10 moles of hydrogen fluoride per mole of reactant is utilized. It has been found that excesses of hydrogen fluoride over this amount usually impart no greater efficiency to the reaction in terms of product yields.

The ratio of pentafluoride to hydrogen fluoride in the catalyst system itself usually ranges from 1–10 moles of hydrogen fluoride per mole of pentafluoride.

The reaction itself may be run at room temperature, and usually can be effected over a range from about 10° C. to about 50° C. Most preferably the temperature of reaction is 10°–30° C.

The reaction itself involving gaseous carbon monoxide is usually run under super atmospheric pressures, usually ranging from about 50 to about 1000 psig. More often the pressure is 100–300 psig.

Again the time of reaction may widely vary depending upon particular reactants, catalyst system, catalyst and reactant ratios etc. However, usually the reaction time is ¼ hour-4 hours.

It is interesting to note that the reaction here is quite specific to the particular catalyst system employed. Many other seemingly similar catalysts, including other Lewis acid catalysts have been found to be ineffective. Thus, for example, systems as aluminum trifluoride/HF, and potassium fluoride/HF when employed did not give appreciable yields of the desired product. Other systems such as fluorinated graphite and acidic resins were also of little use.

In addition, surprisingly the trifluorides of the same three active species here such as $SbF_3$ were completely ineffective and did not yield tolualdehyde from toluene.

The final product is one where predominantly the aldehyde group is para to the alkyl substituent on the benzene ring. However, as is usual in reaction of this type, small amounts of the ortho derivative are also produced.

The invention is further illustrated by the following examples. It is understood, of course, that these examples are merely illustrative and that the invention is not to be limited thereto.

EXAMPLES I–XII

The runs summarized in Table I below in general involve the following reaction scheme. A reactant mixture of toluene and catalyst was charged to a propylene liner having a small weep hole in the top for pressure equilibration. Mixing was accomplished using a teflon coated stirring bar and a magnetic stirrer. The liner and reactants were placed inside a magnetic dash unit which had been modified by removal of the thermal-well, cooling coil and sample tube from the head, and subsequently plugged. The unit was charged to operating pressure from a carbon monoxide supply, mixing was started and timing initiated. Results are given in Table I. All reactions were quenched by addition of cold water, and the organic phase separated and dried with magnesium sulfate. Analysis was by gas chromatograph.

TABLE I

| RUN NO. | TEMP. (°0) | PRESS. (psig) | TIME | CHARGE (g.) TOLUENE | TaF$_5$ | HF | PROD. % TOLUALDEHYDE |
|---|---|---|---|---|---|---|---|
| 1 | 25 | 100 | ½ hr | 1.0 | 3.0 | 0.3 | 70.5 |
| 2 | 25 | 100 | ½ hr | 1.0 | 3.0 | 1.0 | 81.0 |
| 3 | 25 | 100 | ½ hr | 1.0 | 3.0 | 2.0 | 87.1 |
| 4 | 25 | 100 | ½ hr | 1.0 | 3.0 | 3.0 | 85.7 |
| 5 | 25 | 100 | 1 hr | 1.0 | 3.0 | 3.2 | 88.2 |
| 6 | 25 | 100 | ½ hr | 1.0 | 3.2 | 4.1 | 88.4 |
| 7 | 25 | 100 | ¼ hr | 1.0 | 3.0 | 2.0 | 67.9 |
| 8 | 25 | 100 | ¼ hr | 1.0 | 2.0 (NbF$_5$) | 1.0 | 84.6 |
| 9 | 25 | 120 | ½ hr | 2.0 | 7.6 (SbF$_5$) | 5.7 | 61.3 |
| 10 | 25 | 50 | 3 hr | 8.5 | 3.0 | 0.8 | 20.3 |
| 11 | 25 | 300 | 3 hr | 8.5 | 3.0 | 0.6 | 23.7 |
| 12 | 25 | 1000 | 3 hr | 8.5 | 3.0 | 0.6 | 25.3 |

(a) Basis toluene converted.
(b) Selectivity is characteristically 95% para and 5% ortho tolualdehyde.

EXAMPLE XIII

In this example, reactants are mixed in the same manner as that prescribed in Examples I-XII except the system was cooled to 10° C. Tolualdehyde was detected as a product.

EXAMPLE XIV

In this example, reactants are mixed in the same manner as that prescribed in Examples I-XII except the system was heated to 50° C. Tolualdehyde was detected as a product.

We claim:

1. A method for preparing a para-alkyl monosubstituted phenyl aldehyde which comprises the step of reacting under superatmospheric pressure carbon monoxide and an alkyl-substituted benzene in presence of a catalyst comprising hydrogen fluoride and a pentafluoride selected from the group consisting of TaF$_5$, NbF$_5$ and SbF$_5$.

2. The method of claim 1 wherein said pressure is at least 50 psig.

3. The method of claim 2 wherein said reaction is effected at a temperature ranging from about 10°-50° C.

4. The method of claim 1 wherein said alkyl group is a C$_1$-C$_{18}$ group.

5. The method of claim 4 wherein said alkyl group contains 6 carbons or less.

6. The method of claim 1 wherein the mole ratio of pentafluoride to alkyl-substituted benzene is 1-5 moles:1 mole.

7. The method of claim 1 wherein the mole ratio of HF to alkyl-substituted benzene is 5-10 moles:1 mole.

8. The method of claim 1 wherein tolualdehyde is produced from toluene.

9. The method of claim 1 wherein the ratio of pentafluoride to HF is 1 mole:1-10 moles.

* * * * *